(12) United States Patent
Guelat et al.

(10) Patent No.: US 8,075,563 B2
(45) Date of Patent: Dec. 13, 2011

(54) RESURFACING REAMER WITH CUTTING STRUTS

(75) Inventors: Didier Guelat, Porrentruy (CH); André Lechot, Orvin (CH)

(73) Assignee: Greatbatch Medical S.A., Orvin (CH)

( * ) Notice: Subject to any disclaimer, the term of this patent is extended or adjusted under 35 U.S.C. 154(b) by 763 days.

(21) Appl. No.: 12/139,563

(22) Filed: Jun. 16, 2008

(65) Prior Publication Data

US 2008/0300600 A1    Dec. 4, 2008

Related U.S. Application Data

(63) Continuation-in-part of application No. 11/617,743, filed on Dec. 29, 2006, now Pat. No. 7,918,856.

(60) Provisional application No. 60/943,849, filed on Jun. 14, 2007.

(51) Int. Cl.
*A61B 17/00* (2006.01)

(52) U.S. Cl. .................... 606/80; 606/81; 606/89

(58) Field of Classification Search .............. 606/80–82, 606/89
See application file for complete search history.

(56) References Cited

U.S. PATENT DOCUMENTS

| | | | |
|---|---|---|---|
| 2005/0075639 A1 | 4/2005 | Lechot | |
| 2005/0251145 A1 | 11/2005 | Desarzens et al. | |
| 2006/0015111 A1 * | 1/2006 | Fenton | 606/80 |
| 2007/0118137 A1 | 5/2007 | Wolford et al. | |

FOREIGN PATENT DOCUMENTS

| | | |
|---|---|---|
| DE | 20213728 | 12/2002 |
| EP | 0782840 | 7/1997 |
| EP | 1477120 | 11/2004 |
| RU | 2176903 | 12/2001 |
| WO | WO2004032767 | 4/2004 |
| WO | WO2008037984 | 4/2008 |

\* cited by examiner

*Primary Examiner* — Thomas C. Barrett
*Assistant Examiner* — Andrew Yang
(74) *Attorney, Agent, or Firm* — Michael F. Scalise (57) ABSTRACT

Disclosed is a guided orthopedic bone reamer (10a) for cutting a profile relief shape (21a) into a joint bone (20). The reamer (10a) has a cutting head (30a) and an axial guide assembly (70). The cutting head (30a) has a profile cutting form (24a) with a rim (34) and an apex (38a). The apex (38a) connects to the cutting form (24a) by a set of struts (94). An axial guide assembly (70) has one end (44a) fixed to the apex (38a) and at the other end has a bayonet mechanism (76) connectable to a drive handle. Rim cutting teeth (36a) are set into the rim (34) to cut a cylindrical profile (21a), and bevel cutting teeth (96) integral to the struts (94) cut a bevel (25) onto the cylindrical form (21a) cut into the bone (20). A guide pin bore (12a) passes through the apex (38a) and the guide assembly (70) concentric with the axis of rotation (18) to receive a guide pin (14) to guide the reamer (10a) in cutting alignment relative to the joint bone (20) to be cut.

25 Claims, 9 Drawing Sheets

RESURFACING REAMER WITH CUTTING STRUTS

The present application is a Continuation-in-Part and claims the benefit of prior filed U.S. application Ser. No. 11/617,743, filed 29 Dec. 2006, now U.S. Pat. No. 7,918,856 to Guelat et al., and also claims the benefit of prior filed U.S. Provisional application Ser. No. 60/943,849, filed 14 Jun. 2007, which applications are incorporated herein by reference.

FIELD OF THE INVENTION

The present invention is in the field of surgical apparatuses used in the treatment of diseases, wounds and other abnormal conditions of the bodies of humans and lower animal (Class 128). Specifically, the present invention relates to orthopedic instrumentation designed for particular use in a surgical procedure on bone structure to correct a deformity, fracture, unwanted or diseased condition Class 606/subclass 53). More specifically, the present invention relates to a cutting means particularly adapted to assist in the removal of bone tissue (86) on the proximal portion of a femoral head so that a prosthetic member fitted thereto to effect the repair of the bone for purposes of altering or replacing the femoral portion of the hip joint (subclasses 86, 87, 89).

BACKGROUND OF THE INVENTION

The invention relates to a bone shaping system made up of an instrument holder and a surgical instrument, i.e., a surgical tool head, for attachment to the holder. The holder includes a shank equipped with a head designed to receive an instrument, and an annular locking component mounted so as to slide about the shank, under the head, equipped with locking means which cooperate with the head so as to lock the instrument on the head, and pushed against the head by a helical spring. The present surgical tool head is disposed to mate with and attach to the head of the tool holder. An example of a tool holder suitable for practice with the present invention is disclosed in U.S. Patent Application Publication No. 2005/0251145, the content of which is incorporated herein by reference.

One such system is described in European Patent 0782840, the content of which is incorporated herein by reference thereto, and includes a shaft (10), equipped at one end with a cutting head holder (12) which has a bayonet joint and lock. A hemispherical or conical rotary cutting head (1) has inner radial rods (4) to engage with the bayonet joint. The cutting head contains an axial guide tube (5) between the inner ends of the radial rods and a central aperture (3) to receive a twist drill (9) which makes a hole in the middle of the recess formed by the cutting head. The lower end of the guide tube has one or more notches to receive corresponding studs on the twist drill so they rotate together. Other systems provide for reshaping of the bone, but the tool itself generally obstructs the view of the bone lobe during cutting.

A total hip replacement procedure removes the organic stem of a bulbous bone joint replacing it with an artificial one. This is a relatively radical surgical procedure, and alternative processes exist that attempt to preserve the natural joint. One such procedure places a hard, external prosthetic cap over a resurfaced bulbous bone joint. The cap has an external spherical surface which mates with a hip socket. The cap is often made of metal and has precise interface dimensions which must be matched to the bone of the joint in order for the cap to properly fit over the joint, and to properly function in its corresponding prosthetic hip socket. Therefore, there is a need for cutters capable of cutting and shaping the bulbous bone joint in preparation for the reception of a prosthetic cap. Such an application presents other challenges in guidance and control, particularly, that of ensuring that the stem of the bulbous bone joint is not damaged in the process. Still further, what is needed therefore is a system which enables controlled cutting and reshaping of the bulbous bone joint in preparation for the reception of a bone cap prosthesis. In particular, what is needed is a reamer capable of cutting the bulbous bone joint to closely receive a bulbous bone joint prosthetic cap.

SUMMARY OF THE INVENTION

The present invention is a guided orthopedic reamer system which includes a cannulated reamer handle (holder) and a corresponding cannulated reamer tool. The cannulas of the reamer handle and the reamer tool serve as a pilot bearing surfaces. When reamer handle and reamer tool are assembled together, their cannulas are coaxial to enable them to be operated over a drill guide pin received in one or both cannulas. The inner surfaces of the cannulas provide bearing surfaces against which the guide pin is rotatably receivable. The guide pin axially aligns with the stem of the bulbous end of a bone joint being worked on (e.g., the proximal end of a femoral bone head) with the reamer tool and handle, and facilitates the accurate and controlled reshaping of the bulbous bone joint.

The reamer tool is made up of a from cutting portion and a central guide portion with a bar structure. The bar structure includes members which connect to and extend radially from the central guide. Optionally, the central guide includes a stop surface offset from a plane of the bar structure which enables the stop surface to contact an associated surface of the bone, and to control the depth to which the cutting form can plunge into the bone so as to prevent potential damage the bulbous bone end. The offset stop surface is preferably polished to reduce friction during rotation of this surface against the bone at the work site. The offset surface is perpendicular to the axis of the drill pin and the axises of the cannulas of the reamer handle and the reamer tool.

An advantage of the invention is a combination handle and inverted (concave-type) reamer system wherein the reamer tool is a single integrated part which requires fewer operative steps to accomplish an analogous result at a work site relative to other reamer systems. This thereby reduces surgical time and increases precision of the result at the work site over other reamer systems. This result is accomplished by a structural design combining different types of cutting teeth that engage the work site at different angles to provide a work result having multiple surfaces cut in distinctly different plains. Additionally, the design of cutting teeth enables a lower cutting torque and allows cutting on multiple surfaces simultaneously.

Another object of the invention is to provide a guided means of cutting and shaping the bulbous bone of a joint (e.g., a hip joint) to reduce the risk of damaging it in the shaping process. A further object of the invention is to provide a system which enables controlled cutting and reshaping of the bulbous end of a joint bone in preparation for closely receiving a bone joint prosthetic cap.

DETAILED DESCRIPTION OF THE INVENTION

Referring now to the drawings, the details of preferred embodiments of the present invention are graphically and schematically illustrated. Like elements in the drawings are represented by like numbers, and any similar elements are represented by like numbers with a different lower case letter suffix.

Figure 1A:
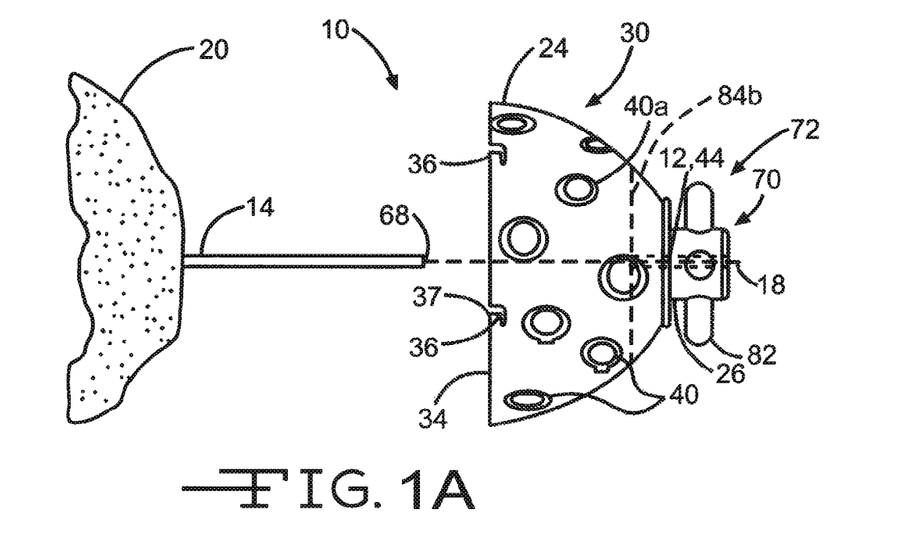
FIG. 1A is a side plan view of a guided reamer of the present invention showing a combination of rim cutting teeth, internal curved-surface cutting teeth, with the reamer disposed to be engaged with a guide pin set in a femur joint.
Figures 1B, 2:
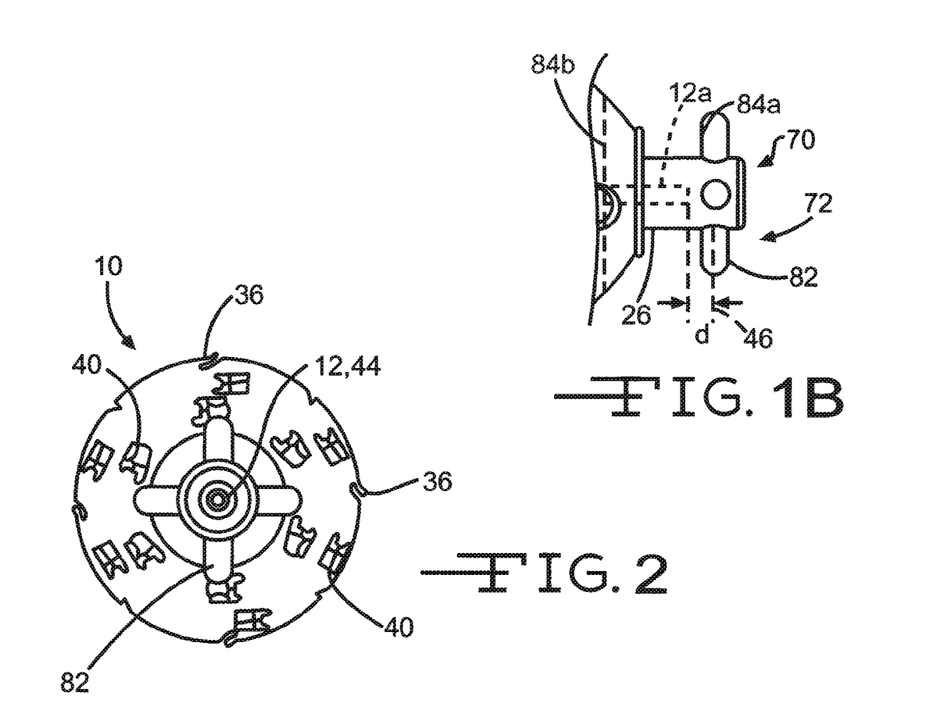
FIG. 1B is a partial side view of the guided reamer surgical tool of FIG. 1, wherein the guide assembly has a blind-ended guide bore to provide a depth of cut stop.
FIG. 2 is a top plan view showing an alternative embodiment of the guided reamer surgical tool head of FIG. 1 with showing alternate inside and outside rim cutting teeth and an alternative curved-surface cutting teeth.
Figure 5A:
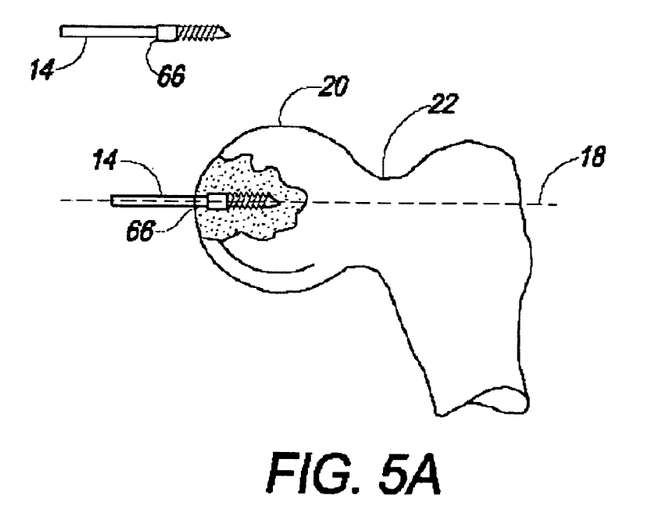
FIGS. 5A and 5B are side views of the stem of bulbus bone joint with a guide pin in place before and after use of the present tool head to shape the stem.
Figure 5B:
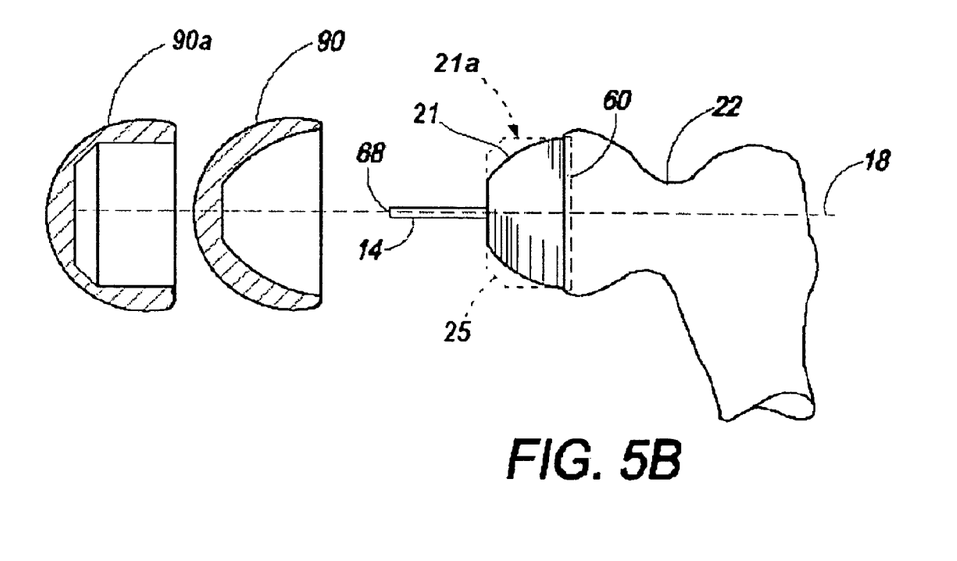

As shown in FIGS. 1A-1B and FIG. 2, the present reamer 10 has a profile cutting head portion 30 and an axial guide assembly 70 portion. The cutting head includes a profile cutting form 24. "Profile cutting form" as used herein means that this portion of the reamer 10 cuts a profile shape or form 21, 21a (see FIG. 5B) in relief into the bone 20, the relief shape projecting from the bone and having a symmetric profile. The cutting form 24 has a cutting rim 34, inner cutting surface 32 and an apex 38a (FIG. 7B). The apex 38a is opposite the cutting rim 34 and concentric with the rotational axis 18 of the reamer 10. The specific profile shape cut into the bone 20 by the reamer 10 is defined by the profile of the inner cutting surface 32 and by the cutting form 24 being provided with a combination of different types of inner surface cutting teeth. The specific profile cutting form 24 chosen by the user is selected to provide a cut shape profile adapted to enable the resurfaced bulbous bone joint 20 to closely mate with a prosthetic cap 90, 90a (e.g., see in FIG. 5B). The present reamer 10 differs from acetabular reamers (not shown) which cut/gouge a concave cavity into a bone joint 20. To wit, the present reamer 10 reshapes the external surfaces of bulbous bone joint 20, rather than gouge a (concave) cavity into the bone. In other words, the present profile cutting reamer cuts the joint 20 so as to maintain a convex cross-section of the bone material at the work site, in contrast to reamers which cut a cavity (concave cross-section) into the bone.

In the embodiment illustrated, the guided reamer 10 has rim cutting teeth 36, 37, and form cutting teeth 40, 40a and plaining teeth 50. In addition to the teachings set forth herein, the form of these teeth may be practiced in the present invention in any of a number of manners known in the art. For example, see US patent publication no. 20050075639, entitled "Contour Reamer Teeth" and US Patent publication no. 20060095041, entitled "Contour Reamer Teeth and Method of Manufacture" (the contents of which are incorporated herein by reference). The teeth of the reamer 10 are adapted to accurately control the shaping of the bulbous bone joint 20 to receive a complementary shaped prosthetic cap 90, 90a (e.g., of a prosthetic hip joint, see FIG. 5B).

Figure 3:
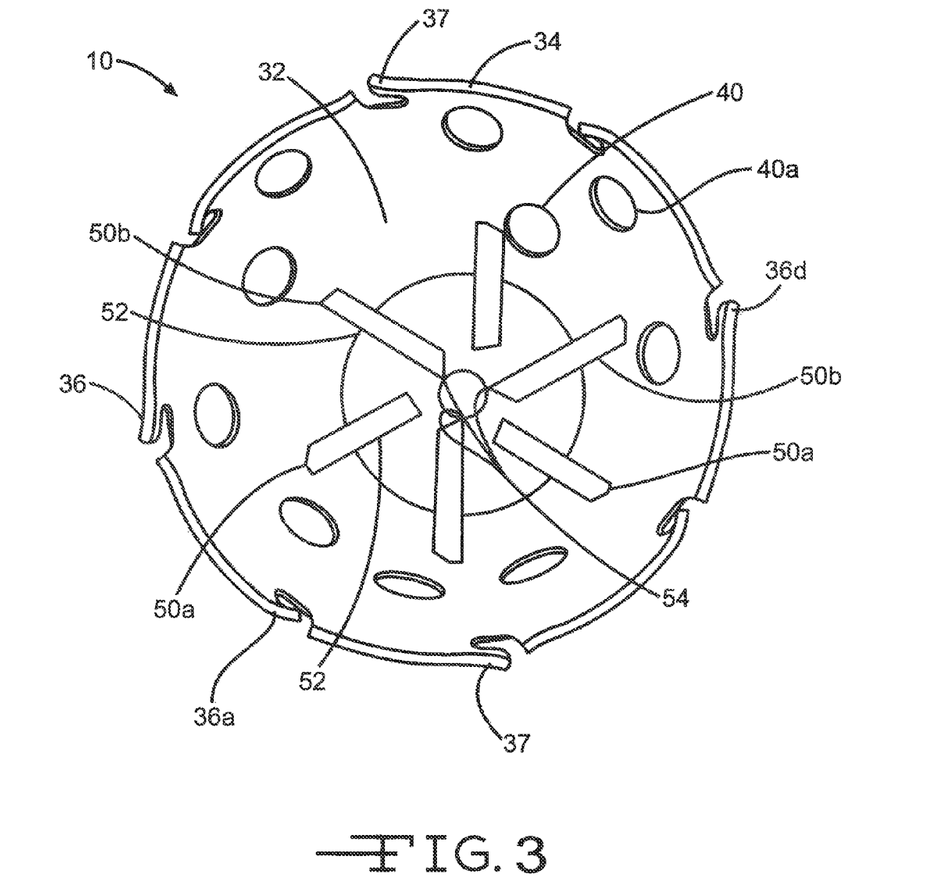
FIG. 3 is a perspective view of the present inverted reamer surgical tool head showing the rim cutting teeth and curved-surface cutting teeth of FIG. 1/2 combined with a set of planar cutting teeth inside the reamer.

In the examples illustrated, the profile cutting form 24 has rim cutting teeth 36, set into the rim 34 of the concave cutting head 30, form/surface cutting teeth 40, 40a disposed in the inside surface 32 of the cutting head 30, and planing teeth 50—also disposed in the inside surface 32 of the cutting head 30 (see FIG. 3). FIG. 3 illustrates two the different types of cutting teeth 36, beyond the more conventional inside surface cutting teeth 40, 40a located on the inside surface 32 of the form cutting body 30 of the reamer 10.

In the preferred embodiment illustrated, the rim cutting teeth 36 are disposed with a pitch to cut either to the outside of the rim 34 and/or to the inside of the rim (see FIG. 3). Also, the rim cutting teeth 36 have a downward cutting face 37 as well (see FIG. 1A). The inside-to-outside pitch of the cutting teeth 36 is important, and is set to permit the rim 34 to cut a leading-edge trough 60 (see FIG. 5B) as the reamer 10 cuts away the surface of the joint bone 20. The capability to cut a leading edge trough 60 may not be needed in every application, but in those where it is useful, the pitch width of the cutting teeth 36 is set to provide a trough 60 disposed to closely receive the thickness of the rim of the prosthetic cap 90, 90a to be fitted to the joint 20. Also note, as shown in FIG. 3, the inside rim cutting teeth 36 are disposed in a relationship with the nearest circle of surface cutting teeth 40, 40a to provide an overlapping cut.

As shown in the preferred embodiment of FIG. 3, the third set of cutting teeth were planing teeth 50, which were set adjacent the apex end boss 44 of the cutting head's interior surface 32. The planing teeth 50 were of two types: the shorted type 50a had a side cutter 52, and the longer type 50b had both a side cutter 52 and an end cutter 54. The end cutter 54 of the long planing teeth 50b provided for trimming away material adjacent the guide pin 14 as the reamer 10 was advanced down the pin 14. The side cutter 52 of both types of planing teeth 50a and 50b provided for flattening the joint 20 adjacent the guide pin 14. The combination of the different cutting features of the reamer 10 provide a formed bulbous joint bone 20 having, for example, characteristics shown in FIG. 5B.

The axial guide assembly 70 portion of the reamer 10 interfaces the body 30 of the profile cutting form 12, 12a with the reamer holder/handle 74. In the embodiment illustrated in FIGS. 1A-1B and 2, the axial guide assembly 70 has a cylindrical boss 26, 26'. An apex boss end 44 of the boss 26, 26' (distal from the handle 74) interfaces with (and may form a part of) the apex 38a (FIG. 7B) of the cutting form 24. The other or handle boss end 45 (proximal to the handle) of the boss 26, 26' is adapted to provide a drive interface 72, the features of which connect the reamer 10 to the handle 74. The axial drive interface 72 is adapted to directly transmit rotational force applied to the handle 74 to the reamer 10 along the axis of rotation 18.

The drive interface 72 includes a bar structure comprised of at least one bar 82, radially extending through the handle end 45 of the boss 26, 26' perpendicular to the axis 18. However, two or more bars 82, preferably, evenly spaced about the boss 26, 26', may also be used. The drive interface 72 is made up of the handle end 45 of the boss 26, 26', with bars 32 attached thereto which are axially spaced apart and which extend radially out from the post.

The boss 26, 26' of the guide assembly 70 includes has a central guide or pilot pin bore (cannula) 12, 12a. The pilot bore cannula 12, 12a is concentric with and defines the axis 18 of rotation of the reamer 10. The pin bore 12, 12' is adapted to receive a drill/guide pin 14 secured in an appropriate manner in the bulbous end 20 of a joint bone (e.g., the femur or the humerus bone in a manner appropriately aligned with the bone stem 22, see FIG. 5A). In a preferred embodiment, the present reamer 10 is assembled in combination with a reamer handle 74 (see FIGS. 4A-4C). The combination reamer handle 74 and reamer head 10 is rotatable over the guide pin 14 affixed securely in the bone joint 20 in a manner known in the art. An appropriately installed guide pin 14 axially aligns the guide pin bore 12, 12a in the reamer tool 10 and in an appropriate orientation with the joint bone 20. The guide pin bore 12 can be a through bore as in FIG. 1A, or alternatively can be a blind hole 12a as in FIG. 1B. The cannulation 12, 12a is sized and surface treated to be a close, sliding fit for receiving the drill pin 14, in order to provide appropriate axial guidance to the reamer 10 when cutting bone 20.

A user of the present invention can establish a reference plane 60 at the work site that defines the depth limit that the reamer 10 is to cut into the joint bone 20. The present invention includes a number of alternative features that can alone or in combination meet accomplish a depth of cut limitation. For example, as illustrated in FIG. 1B, the guide assembly 70 can include a stop surface or stop seat 84a in the pilot pin bore 12a that limits the distance that the pin end 68 of the guide pin 14 can travel into the pilot pin bore 12a after the reamer 10 contacts the work surface. The user sets this limitation by installing the pilot pin 14 in the work site perpendicular to the reference plane 60, and allowing the pilot pin 14 to protrude from the uncut surface of the work site a desired length L, relative to the depth d of the pilot pin bore 12a. The depth of cut is limited by the pin end 68 contacting the stop seat 84a.

In another example of depth of cut limitation, the reamer body 30 includes an inner offset surface 84b perpendicular to the axis of rotation 18 defined by the end cutter 54 portion of the long planing teeth 50b, and the pilot pin 14 having a stop-shoulder 66. See FIGS. 1A and 5A. In this embodiment, the stop-shoulder 66 of the guide pin 14 prevents the reamer 10 from cutting too deeply into the joint bone 20. This is accomplished by the end cutter 54 portion of the long planing teeth 50b coming against the stop-shoulder 66 and being prevented from sliding further down the guide pin 14. In this case, the shoulder 66 of the guide pin 14 is set to the desired maximum depth of the cut upon its installation in the joint 20 by the user. The offset surface 84b is preferably polished to reduce friction during relative rotational movement between this surface 84 and the surface 68 referenced to the bone 20. By either of these and related means, the cutting form 24 can be prevented from plunging too far into the bone as to potentially damage the bulbous bone stem 22 or to cut more bone away than required to fit the prostheses 90, 90a.

Figure 7A:
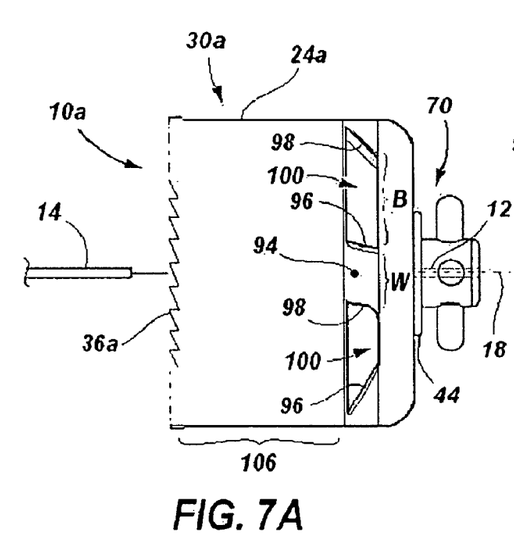
FIG. 7A is a side plan view of a alternative embodiment of the self-guided reamer with rim cutting teeth of the present invention, with the reamer disposed to be engaged with a guide pin set in a femur joint.
Figure 7B:
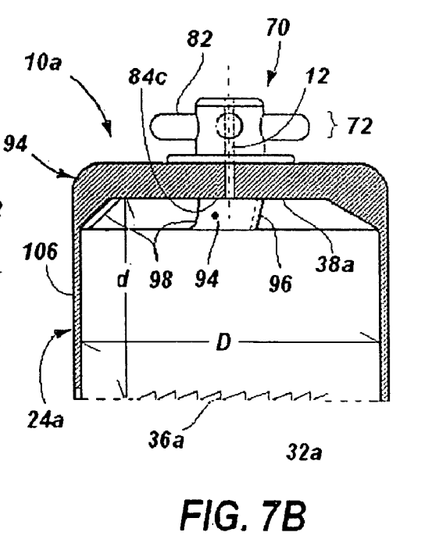
FIG. 7B is a partial cross-sectional side plan view of the self-guided reamer surgical tool head of FIG. 7A.
Figure 8A:
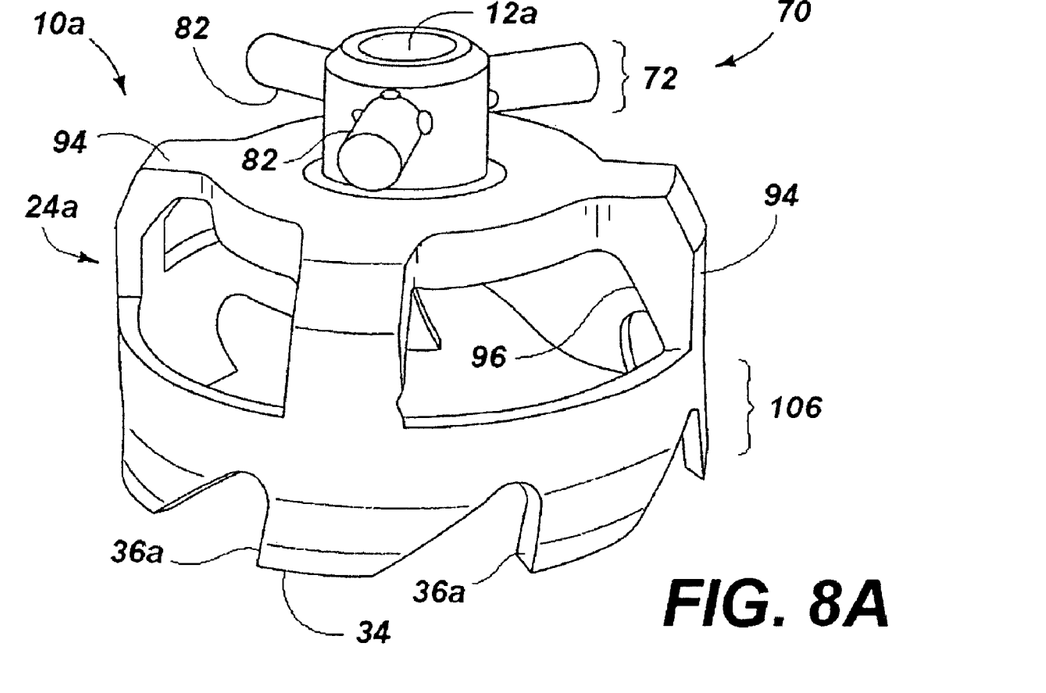
FIG. 8A is a perspective view exemplifying an alternative embodiment of the self-guiding reamer tool of the present invention.
Figure 8B:
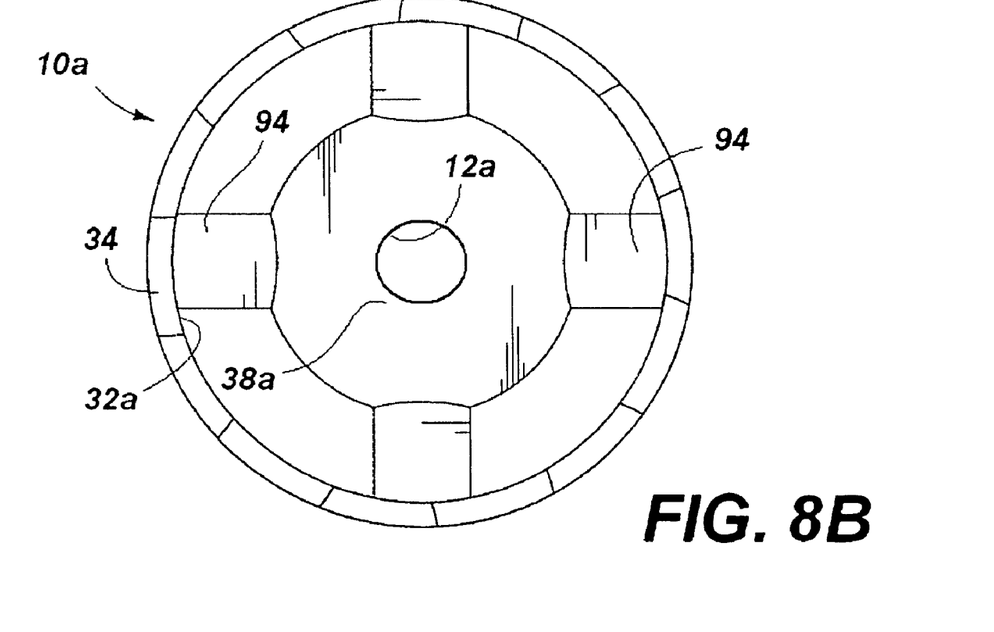
FIG. 8B is a bottom plan view of the reamer tool of FIG. 8A.
Figure 8C:
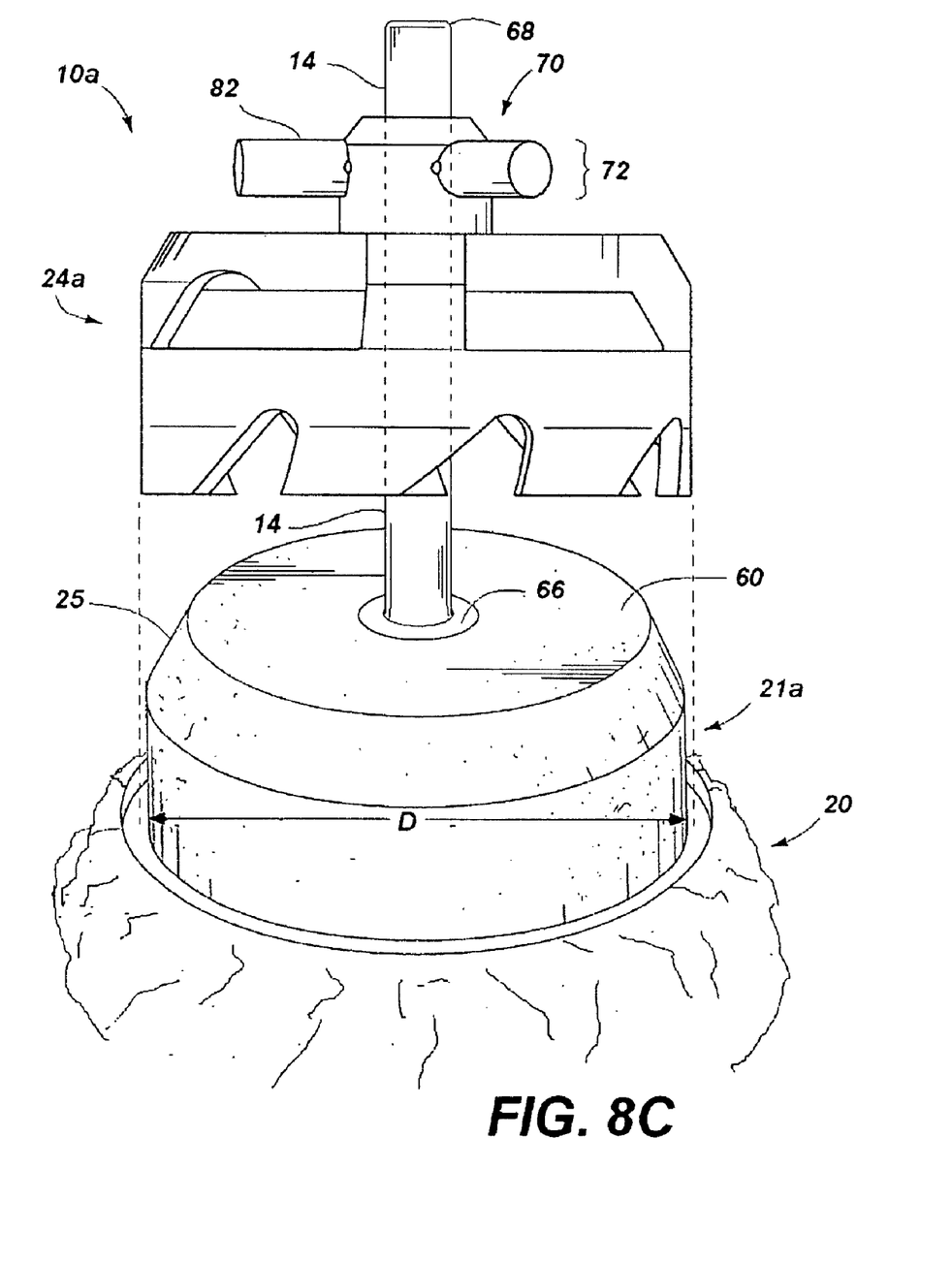
FIG. 8C is a perspective view showing the self-guiding reamer tool 10a being used to provide the chamfered portion 25 of a clindrical form 21a cut into bone 20

Illustrated in FIGS. 7A and 7B, is an alternative preferred embodiment, the self-guiding reamer tool 10a of the present invention which also includes a cutting 30a and an axial guide assembly 70. The cutting head includes a profile cutting form 24a. As can be seen in FIG. 7B, the axial guide assembly 70 of the self-guided reamer tool 10a is substantially the same as described above. The self-guiding reamer 10a has a profile cutting form 24a for cutting a shape in the bone having a substantially cylindrical cross-section. The cylindrical shape is defined by the cutting form 24a having a cylindrical inside surface 32a (shown in FIG. 7B). The depth d of the cylindrical inside surface 32a also provides the self-guiding feature of this reamer tool 10a as the depth the tool 10a cuts into the bone 20 increase. The self-guiding reamer tool 10a provides a specific cut form configured to enable the bulbous bone joint 20 to closely mate with a prosthetic cap 90a (shown in FIG. 5B). The self-guided reamer tool 10a has edge cutting teeth 36a set into the rim 34a of the cutting form 24a. The edge cutting teeth 36a can be with or without pitch to cut parallel, outside and/or inside of the tangential plane of the inside surface 32a. Preferable, the edge cutting teeth 36a are without pitch and/or have outside pitch. Additionally, the self-guiding reamer tool 10a has second set of bevel cutting teeth (or edges) 96 integral to the struts 94 as described below. The bevel cutting teeth 96 provide the chamfered portion 25 of the cylindrical form 21a cut into the bone 20. The benefits of the form or shape 102 (see FIGS. 5B and 8C) are known to one of skill in the art, for example, the relatively greater surface contact area 21a of the self-guiding reamer tool 10a. The rim cutting teeth 36a are disposed to cut the cylindrical form 21a into the bone 20 having an outside diameter substantially equal to the inside diameter D of cylindrical portion of the cutting form 24a, allowing a cut bone wall to serve as an additional guide for the bone reamer 10a.

Interestingly, the present self-guiding reamer tool exhibited unexpected benefits when actually tested. Specifically, "chattering" of the reamer tool 10a was reduced compared with other reamer tools having similar rim cutting teeth. The source of this benefit appears to reside in certain structural features of the cutting form 24a of the self-guiding reamer tool 24a. Specifically, the benefit lies at least in part in the struts 94 that attach the cylindrical portion 106 of the cutting form 24a to the axial guide assembly portion 70 of the reamer tool 10a. The struts 94 have a leading edge bevel cutting tooth 96 and a trailing edge 98, relative to the direction of rotation when cutting. Between the struts 94 is a large clean-out port 100 through which debris generated by the operation of the reamer tool 10 on the bone 20 can pass from within the inside surface 32a to the outside of the reamer tool 10a. The breadth B of the clean-out port 100 is large relative to the width W of the struts 94 to readily eliminate the cutting debris reduce heat accumulation. Additionally, the struts 94 and the apex are relatively massive compared to what is reasonable merely accommodating the mechanical (rotational) stress requirement (see FIG. 7B, a partial cross-sectional side plan view of the self-guided reamer surgical tool showing the thickness of the struts 94 relative to the thickness of the cylindrical portion 106 of the cutting form 24a). This mass acts as a sink and facilitates removing heat from the work surfaces.

Figure 4A:
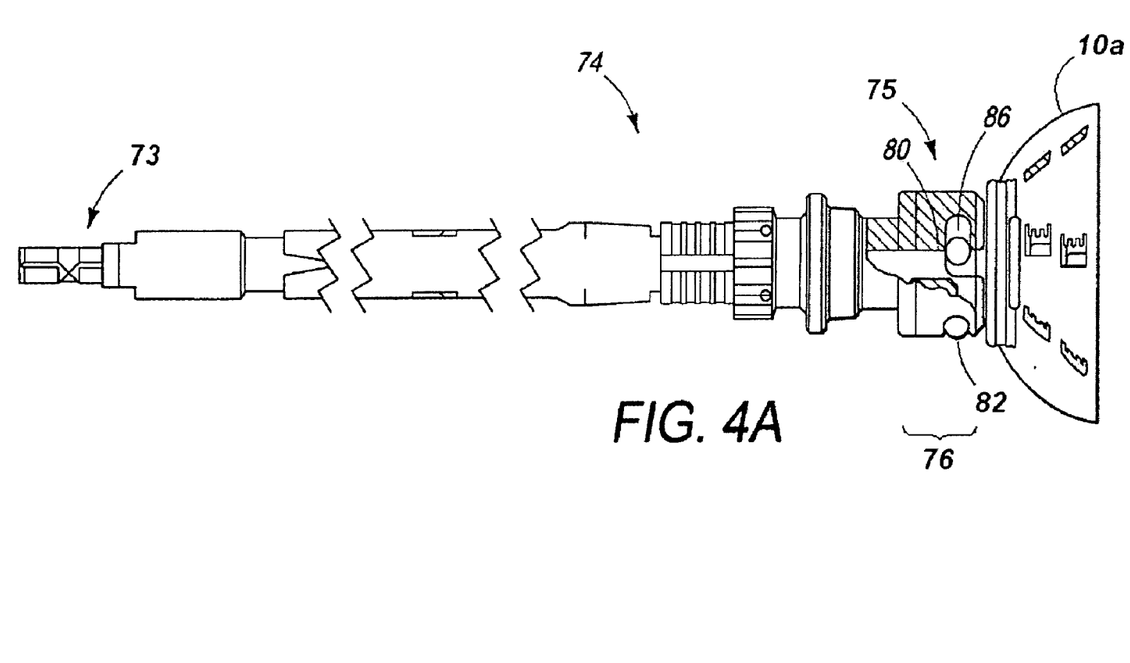
FIG. 4A is a side view of the cannulated reamer handle and reamer tool of the present guided orthopedic reamer system disposed to receive the guide pin at operative work site.
Figure 4B:
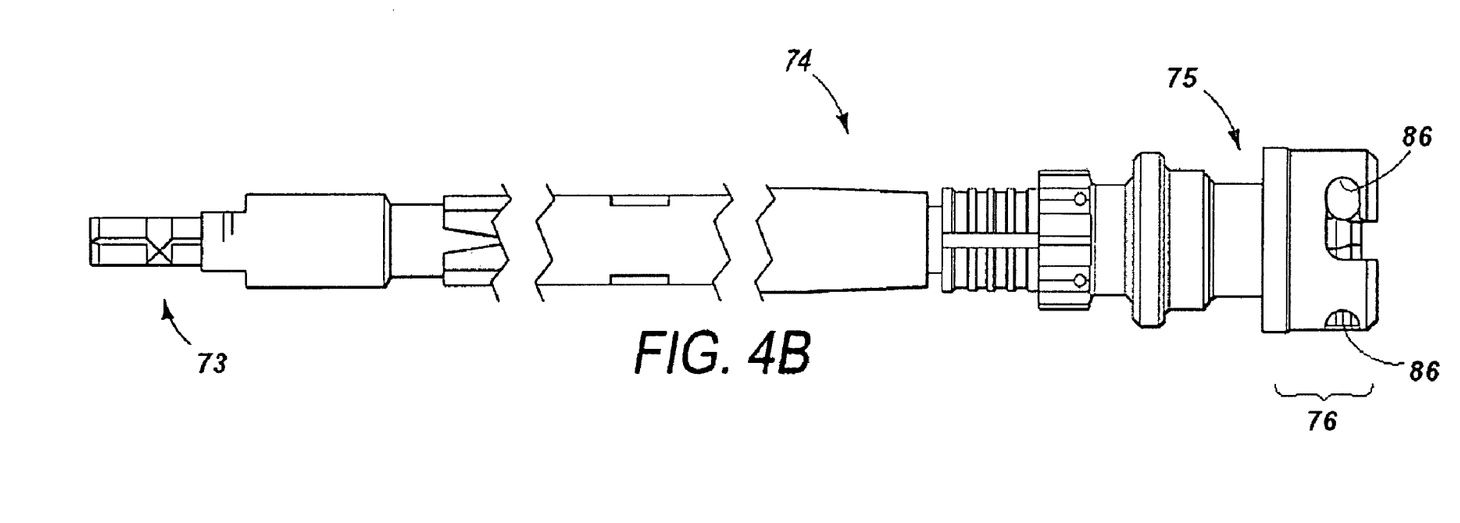
FIG. 4B is a side view of the reamer handle/holder of the present system.
Figure 4C:
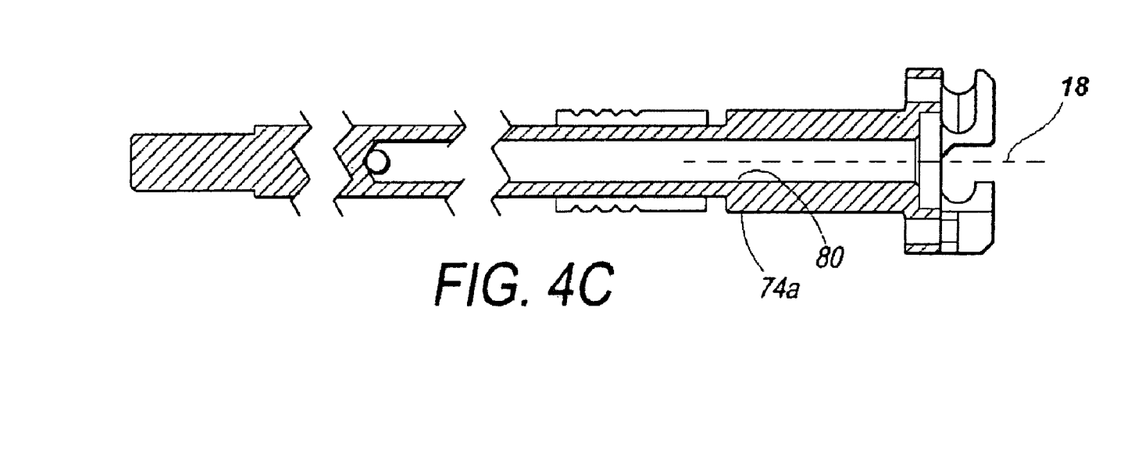
FIG. 4C is a cross-sectional side view of the shaft of the holder of the system of the invention.

Referring now to FIGS. 4A to 4C, the reamer 10, 10a is adapted to be supported by a reamer handle 74. The handle 74 has a first drive end 73 adapted to be attached to a rotational means (not shown). The handle 74 has a second tool attachment end 75 at which is disposed a bayonet-type locking mechanism 76. The locking mechanism 76 is adapted to securely attaching the handle 74 to the drive interface 72 of the reamer 10, 10a. Optionally, the handle 74 has a corresponding shaft cannulation 80, permitting the drill pin 14 to pass at least part way into it should this be necessary. The bayonet locking mechanism 76 includes recesses 86 which engage portions of the bar structures 82 (of the drive interface 72) to securely attach the handle 74 to the reamer 10, 10a.

The drive interface 72 of the guide assembly 70 has bars 82, such as those disclosed in US Patent publication 2005/0251145 (the content of which is incorporated herein by reference), which enable the attachment of the reamer tool 10, 10a to the tool handle 74, and to properly align the cutting features of the tool head 24, 24a with the bulbous joint bone 20. However, other attachment features are known to and are adaptable by one of ordinary skill in the art for practice in the present invention. Alignment is accomplished by the guide assembly 70 having an axial guide bore 12 sharing a common axis 18 with the domed cutting head 30. The axial guide bore 12 passes through the cutting head 30 and the guide assembly 70. In an alternative embodiment shown in FIG. 1B, the guide bore 12a is blind-ended as an alternative means of preventing the reamer 10, 10a from cutting too deeply into the joint bone 20 as described above.

Figure 6:
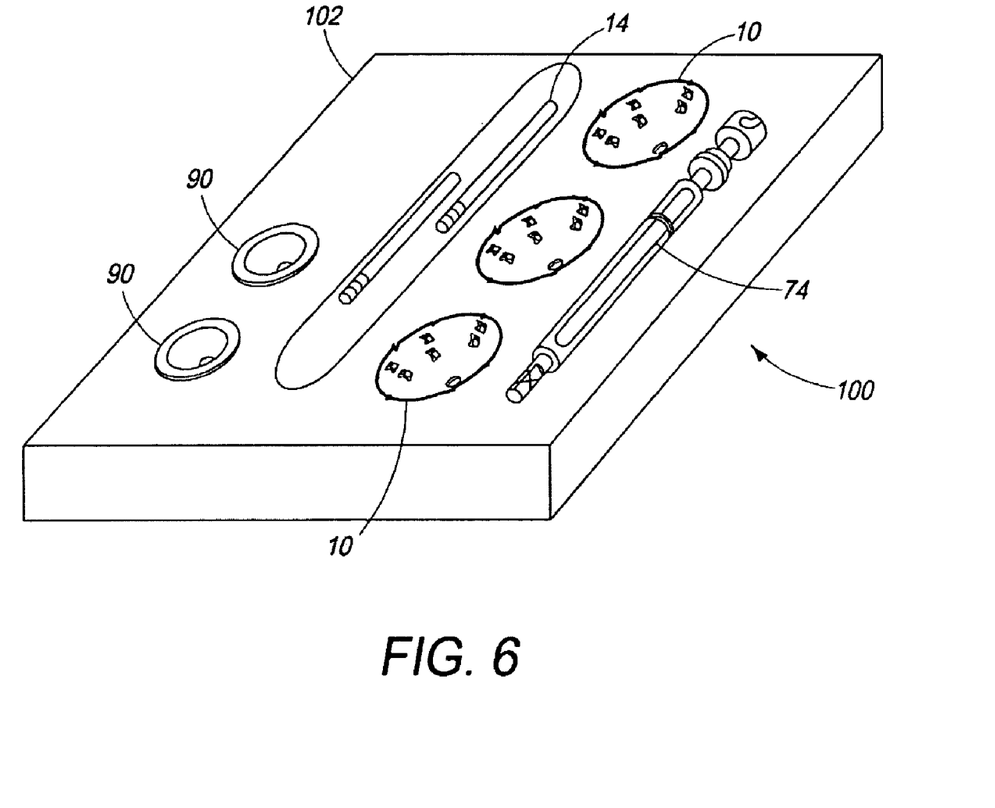
FIG. 6 is a perspective view of a tool kit of the invention.

Referring now to FIG. 6, a tool kit 100 is provided for cutting a defined profile suitable for mounting a prosthesis 90, 90a. The kit 100 includes at least one reamer 10, 10a, a reamer holder 74 capable of imparting torque to the at least one reamer; at least one guide pin 14 adapted to be received in a cannulation 12, 12a of the reamer, optionally, at least one prosthesis 90, 90a; and a case 102 for containing components of the kit.

While the above description contains many specifics, these should not be construed as limitations on the scope of the invention, but rather as exemplifications of one or another preferred embodiment thereof. Many other variations are possible, which would be obvious to one skilled in the art. Accordingly, the scope of the invention should be determined by the scope of the appended claims and their equivalents, and not just by the embodiments.

What is claimed is:

1. A reamer, which comprises:
    a) a cylindrically-shaped cutting form having a constant diameter perpendicular to and extending along a longitudinal axis thereof from a proximal cutting form portion to a distal cutting rim provided with a plurality of distal cutting teeth;
    b) at least two struts spaced about and disposed at an acute angle with respect to the longitudinal axis, wherein there is open area intermediate adjacent struts connecting between the proximal cutting form portion and a base;
    c) an axial guide having a guide length extending from a distal guide end connected to the base to a proximal guide end, wherein an open cannulation passes through the axial guide from the distal guide end to and through the proximal guide end; and
    d) at least two radial bars, each having a proximal radial bar end attached to the axial guide and a distal radial bar end that is not connected to either the axial guide or the cutting form.

2. The reamer of claim 1 wherein the struts have bevel cutting teeth integral to edges of the struts.

3. The reamer of claim 1 wherein the distal cutting teeth are disposed to cut the cylindrical form with an outside diameter (D) substantially equal to an inside diameter (D) of the profile cutting form.

4. The reamer of claim 1 wherein each of the distal cutting teeth comprise a cutting face spaced from an immediately adjacent section of the distal rim in a forward, cutting direction by a relief space.

5. The reamer of claim 1 wherein the distal cutting teeth alternate in pitch such that when viewed in the forward, cutting direction, a first one of the distal cutting teeth cuts beyond the outside surface of the cutting form with the next one cutting beyond the inside surface of the cutting form.

6. The reamer of claim 4 wherein the cutting face of each distal cutting tooth is oriented such that at least a portion of the face extends either outwardly or inwardly, as the case may be, from an imaginary outer or inner periphery of the circumferentially-shaped cutting form defined by a continuum of respective outer and inner radii extending from the longitudinal axis to the distal cutting rim of the cutting form.

7. The reamer of claim 6 wherein in addition to the cutting face of each distal cutting tooth being oriented either in an outwardly or an inwardly direction, each cutting face slopes in a distal direction extending past an imaginary plane defined by the immediately adjacent sections of the distal cutting rim forward of each distal cutting tooth.

8. The reamer of claim 1 wherein there are four radial bars disposed at 90° with respect to each other extending outwardly from the axial guide.

9. The reamer of claim 1 wherein the at least two radial bars extend in a plane at an intermediate location between the proximal guide end and the distal guide end.

10. The reamer of claim 1 wherein the cutting form includes a plurality of wall cutting teeth formed in the cylinder thereof.

11. The reamer of claim 1 wherein an axis of the open cannulation of the axial guide defines a common axis with the longitudinal axis of the cutting form.

12. The reamer of claim 1 wherein the open cannulation in the axial guide is sized and surface treated to be a precise, sliding fit with a drill pin.

13. The reamer of claim 1 wherein the distal guide end includes a contact surface in a plane parallel to a plane of the at least two radial bars, wherein the contact surface prevents the cutting form from plunging so far over a bone as to potentially damage the bone stem.

14. The reamer of claim 13 wherein the contact surface is polished to reduce friction during relative rotational movement against a bone.

15. A tool kit for cutting a defined profile suitable for mounting a prosthesis, the kit including:
    a) at least one reamer according to claim 1;
    b) a reamer holder capable of imparting torque to the at least one reamer;
    c) at least one guide pin adapted to be received in the cannulation that passes from the proximal guide end to and through the distal guide end connected to the base of the reamer;
    d) at least one prosthesis; and
    e) a case for organizing components of the kit.

16. A reamer system, which comprises:
    a) a reamer, comprising:
        i) a cylindrically-shaped cutting form having a constant diameter perpendicular to and extending along a longitudinal axis thereof from a proximal cutting form portion to a distal cutting rim provided with a plurality of distal cutting teeth;
        ii) at least two struts spaced about and disposed at an acute angle with respect to the longitudinal axis, wherein there is open area intermediate adjacent struts connecting between the proximal cutting form portion and a base;
        iii) an axial guide having a guide length extending from a distal guide end connected to the base to a proximal guide end, wherein an open cannulation passes through the axial guide from the distal guide end to and through the proximal guide end; and iv) at least two radial bars, each having a proximal radial bar end attached to the axial guide and a distal radial bar end that is not connected to either the axial guide or the cutting form; and b) a reamer holder having a bayonet locking mechanism capable of locking the holder to the reamer at the radial bars.

17. The reamer system of claim 16 wherein each of the distal cutting teeth comprise a cutting face spaced from an immediately adjacent section of the distal rim in a forward, cutting direction by a relief space.

18. The reamer system of claim 17 wherein the cutting face of each distal cutting tooth is oriented such that at least a portion of the face extends either outwardly or inwardly, as the case may be, from an imaginary outer or inner periphery of the circumferentially-shaped cutting form defined by a continuum of respective outer and inner radii extending from the longitudinal axis to the distal cutting rim of the cutting form.

19. The reamer system of claim 16 wherein the distal cutting teeth alternate in pitch such that when viewed in the forward, cutting direction, a first one of the distal cutting teeth cuts beyond the outside surface of the cutting form with the next one cutting beyond the inside surface of the cutting form.

20. The reamer system of claim 19 wherein in addition to the cutting face of each distal cutting tooth being oriented either in an outwardly or an inwardly direction, each cutting face slopes in a distal direction extending past an imaginary plane defined by the immediately adjacent sections of the distal cutting rim forward of each distal cutting tooth.

21. The reamer system of claim 16 wherein the bayonet locking mechanism includes recesses which catch portions of the bars.

22. The reamer system of claim 16 wherein the open cannulation permits a drill pin to pass therethrough.

23. The reamer system of claim 16 wherein the cannulation in the axial guide is sized and surface treated to be in a precise, sliding fit with a drill pin.

24. The reamer system of claim 16 wherein the cutting form of the reamer includes a plurality of wall cutting teeth.

25. The reamer system of claim 16 wherein the struts have bevel cutting teeth integral to edges of the struts.

* * * * *